United States Patent
Harney et al.

(10) Patent No.: US 7,587,395 B2
(45) Date of Patent: Sep. 8, 2009

(54) SYSTEM AND METHOD FOR PROVIDING PROFILE MATCHING WITH AN UNSTRUCTURED DOCUMENT

(76) Inventors: John Harney, 9 Enfield La., Kings Park, NY (US) 11754; Janet Dwyer, 9 Enfield La., Kings Park, NY (US) 11754

( * ) Notice: Subject to any disclaimer, the term of this patent is extended or adjusted under 35 U.S.C. 154(b) by 383 days.

(21) Appl. No.: 11/190,354

(22) Filed: Jul. 27, 2005

(65) Prior Publication Data
US 2007/0027859 A1 Feb. 1, 2007

(51) Int. Cl.
*G06F 17/30* (2006.01)
(52) U.S. Cl. .......................... 707/6; 707/100
(58) Field of Classification Search ............... 707/2–6, 707/100; 715/200, 210
See application file for complete search history.

(56) References Cited

U.S. PATENT DOCUMENTS

| | | | |
|---|---|---|---|
| 5,664,109 A | 9/1997 | Johnson et al. | |
| 5,832,497 A | 11/1998 | Taylor | |
| 6,363,379 B1 * | 3/2002 | Jacobson et al. | 707/5 |
| 6,529,597 B1 | 3/2003 | Barrett | |
| 6,662,194 B1 | 12/2003 | Joao | |
| 6,681,223 B1 | 1/2004 | Sundaresan | |
| 6,735,568 B1 | 5/2004 | Buckwalter et al. | |
| 2002/0065814 A1 | 5/2002 | Okamoto et al. | |
| 2004/0039734 A1 * | 2/2004 | Judd et al. | 707/3 |
| 2004/0093331 A1 | 5/2004 | Garner et al. | |

OTHER PUBLICATIONS

PCT: Notification of Transmittal of the International Search Report for PCT/US06/28744. Dated Feb. 1, 2008. (3 pages).
PCT: Written Opinion of the International Searching Authority for PCT/US06/28744. Dated Feb. 1, 2008. (4 pages).

* cited by examiner

*Primary Examiner*—Cheryl Lewis
(74) *Attorney, Agent, or Firm*—Keisey, Tutunjian & Bitetto, P.C.

(57) ABSTRACT

A method, system, and computer program product are disclosed for automatically matching the profile of unstructured electronic documents to objective sets of criteria. The is accomplished by evaluating text in the documents, comparing it to a set of weighted keyword criteria, generating a rating based on adherence to the criteria, rating and categorizing the results, sorting and viewing the results based on user defined criteria.

15 Claims, 3 Drawing Sheets

SYSTEM AND METHOD FOR PROVIDING PROFILE MATCHING WITH AN UNSTRUCTURED DOCUMENT

BACKGROUND

1. Technical Field

The present invention relates generally to the field of electronic document evaluation, and more specifically to a system and method for rating the applicability of a specified list of attributes to an electronic document implemented through an attribute weighting, ranking and sorting system.

2. Description of the Related Art

Generally, electronic documents are created in a natural language format, for example, resumes, online dating profiles, recipes versus ingredients etc. This unstructured format often requires time consuming user evaluation of the document.

In order to automate an electronic system for evaluating a large number of unstructured electronic documents, a user must define a set of rules for use in determining the suitability or applicability of a document to a set of criteria. The flexible nature of the English language makes defining such rules difficult.

Most commonly, an automated system may be used to collect the electronic documents, but a user must then read each document to evaluate the document's applicability to a set of criteria.

Another commonly used system requires the use of structured documents. Users are frequently presented with a software interface containing multiple discrete entry fields. Users are then asked to fill out each entry field with information from their document.

Regarding the prior art, the most current implementations of electronic document profile matching require a structured document. For example, U.S. Pat. No. 6,691,223, issued Jan. 20, 2004 to Sundaresan, discloses a system allowing a user to match indices in an XML document to a target document.

XML, or Extensible Markup Language, is a strictly defined set of rules for representing data in electronic documents. The XML format allows documents to be read by a wide variety of computing systems, without regard for differences in operating system, hardware, and software dependencies. The limitation of this system is that the target document must be formatted in a structured manner.

Additional implementations of electronic profile comparison currently require large amounts of data input. U.S. Pat. No. 6,735,568, issued May 11, 2004 to Buckwalter, et al., discloses a "Method and system for identifying people who are likely to have a successful relationship". However, this invention requires users to answer an extensive set of quesstions in order build an electronic profile.

Currently in the art, a problem exists where a large number of unstructured electronic documents must be evaluated against an objective set of criteria. For example, in employment recruiting, it is common to receive over 500 new resumes for a single job position with generally available skill requirements. Additionally, when searching through previously stored resumes, only 100 out of 10000 (1%) of received resumes, on average, will match a given position. Within the 100 received resumes matching a given position, approximately 20 qualified candidates must be personally interviewed by an employment agency or corporate HR department to find a single candidate right for a particular job.

The task of paring down a large number of candidate resumes typically requires an employment recruiter to manually search job sites and stored resumes, where the recruiter must read and evaluate each resume, or to recall previous candidate resumes from memory. Some particularly organized employment recruiting companies have been able to categorize and store candidate resume data. However, this requires gathering copious amounts of information by manually reading resumes and interviewing candidates in person, by telephone or through structured web based forms.

It becomes apparent from the foregoing that a need exists for an automated method of analyzing large volumes of unstructured documents to generate a list of documents that closely matches a desired profile.

SUMMARY OF THE INVENTION

A method for providing profile matches in unstructured documents is disclosed. The profile matching includes defining a set of requirements, or criteria, to be met by the unstructured electronic documents, loading a document, comparing the document against the predefined requirements, and ranking the unstructured documents based on the level of conformity to the requirements. The requirements include scanning electronic documents for words and phrases, and analyzing statistics related to the appearance of keywords and phrases in the target document. Lists of keywords and phrases may be expanded to use synonyms or other related phrases. Ranking includes assigning point values to generate profile scores for each document based on matching the predefined criteria. One or more scores may be assigned to indicate matches of criteria in different categories. Ranking also includes categorizing and sorting documents based on their profile scores.

BRIEF DESCRIPTION OF DRAWINGS

The disclosure will provide details in the following description of preferred embodiments with reference to the following figures wherein.

DETAILED DESCRIPTION OF PREFFERED EMBODIMENTS

Figure 1:
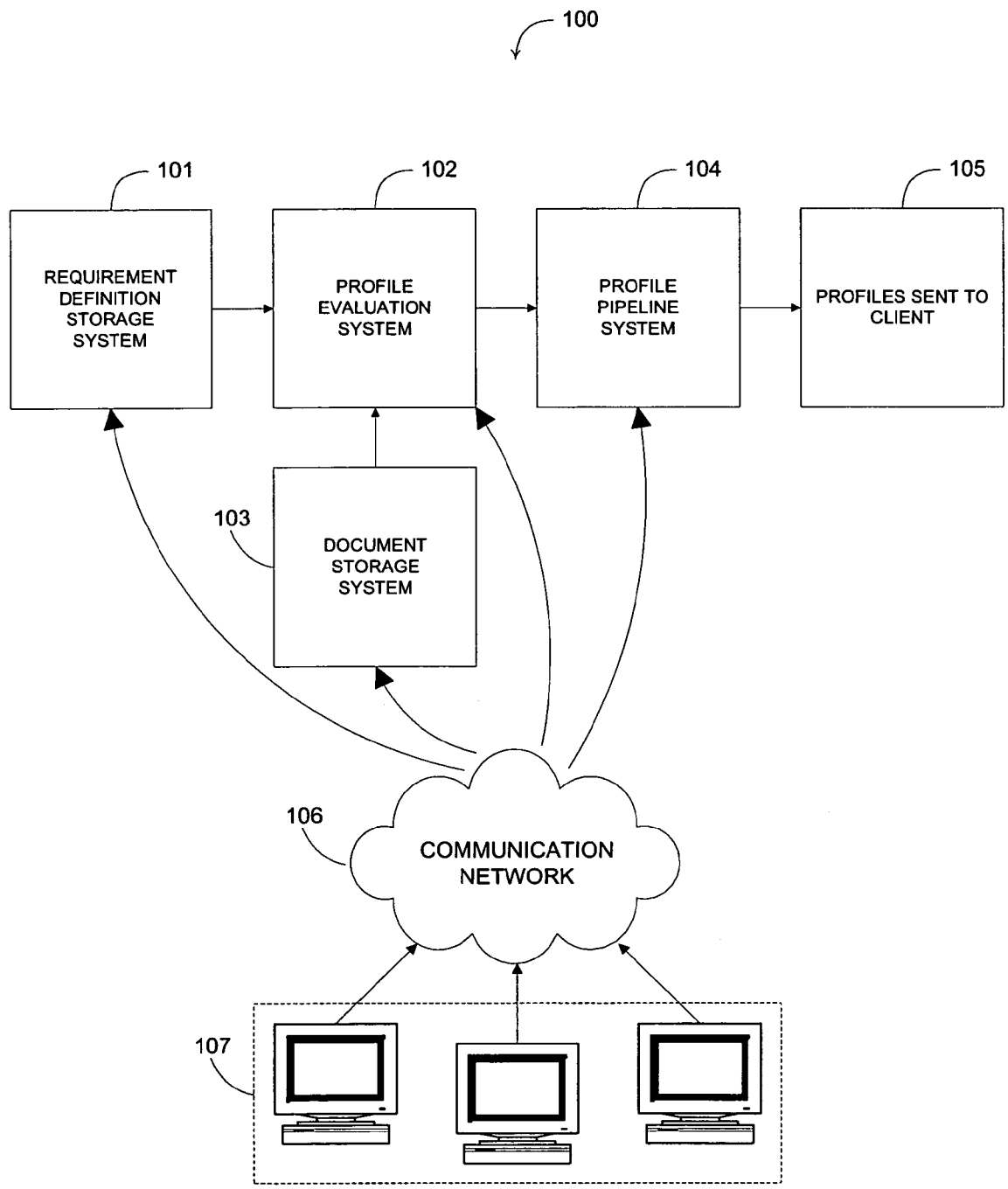
FIG. 1 is a block diagram of the general structure of an unstructured profile matching system.
Figure 2:
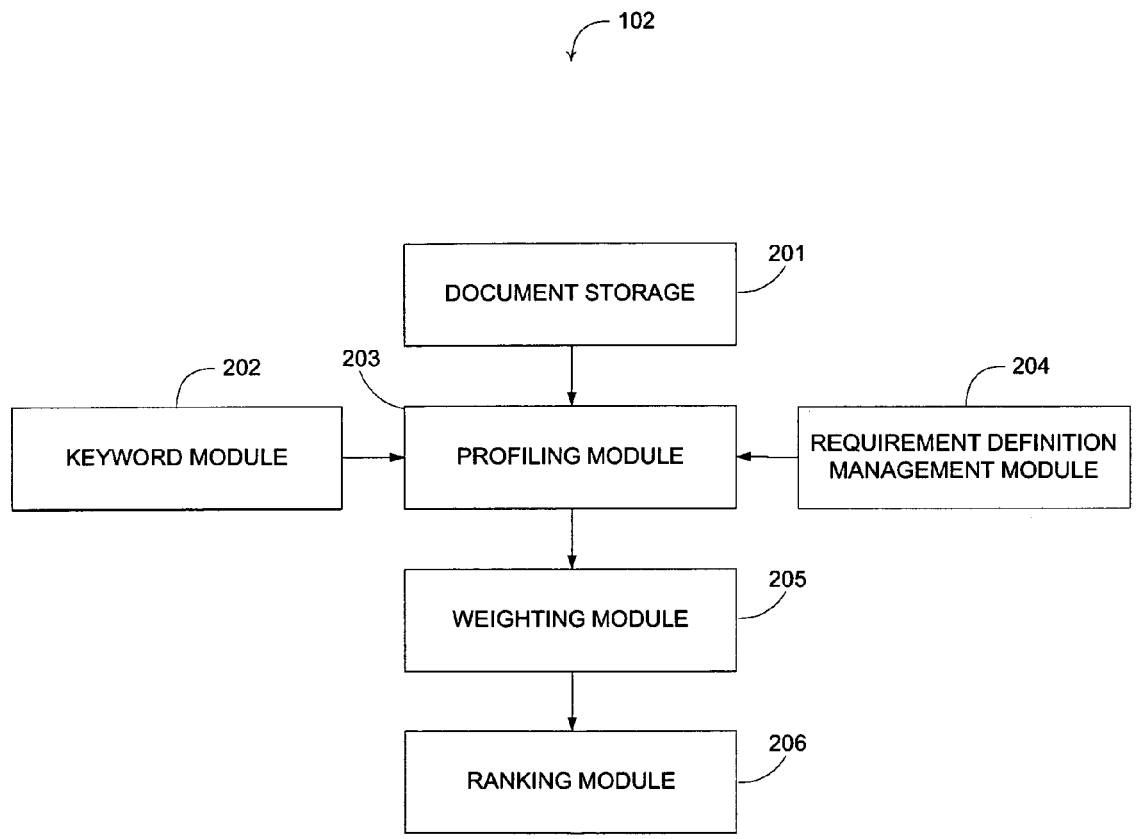
FIG. 2 is a block/flow diagram showing a general overview of the profile evaluation system.
Figure 3:
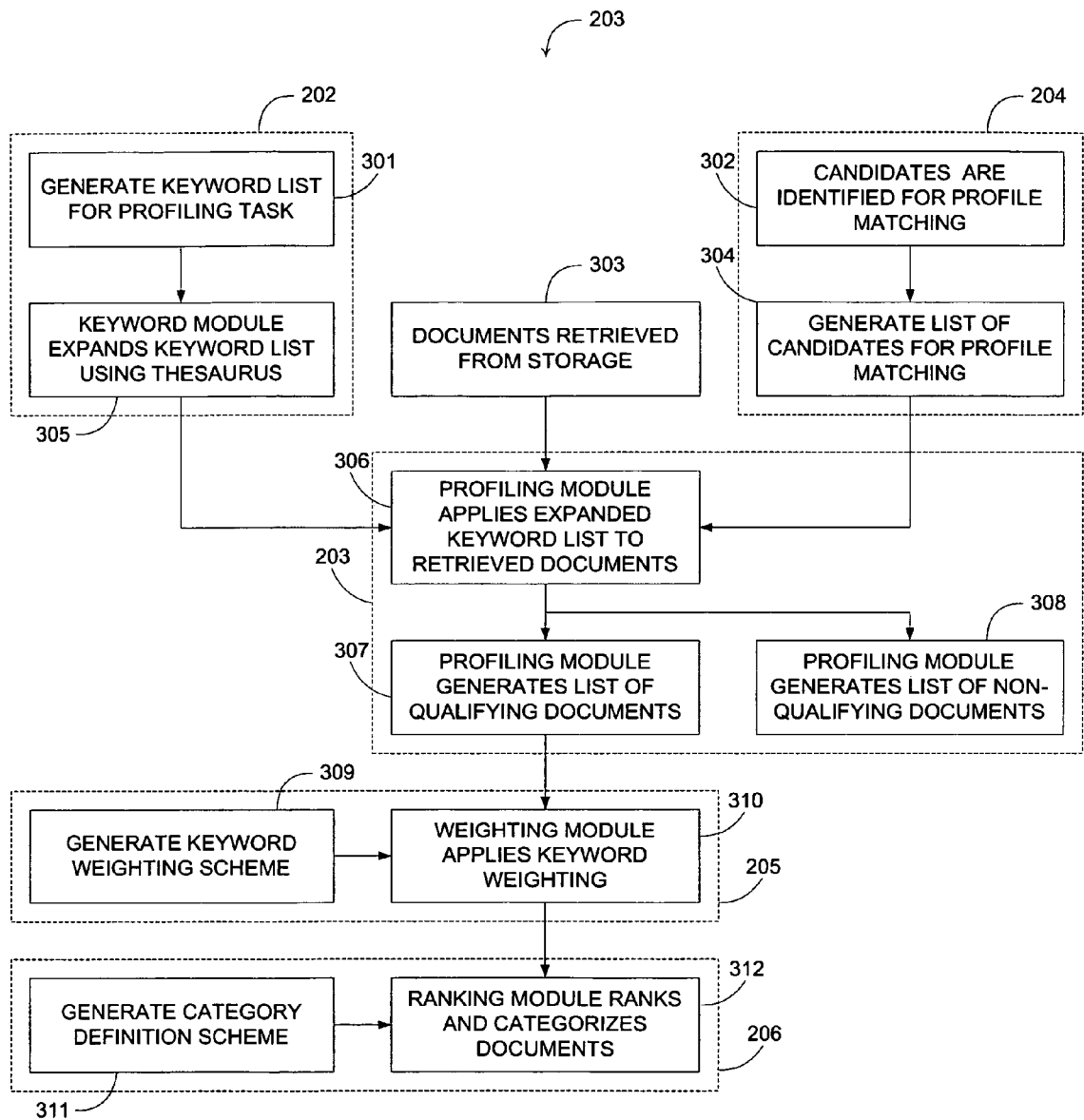
FIG. 3 is a block/flow diagram detailing the process for rating, categorizing and sorting profile matches.

It should be understood that the elements shown in FIGS. 1-3 may be implemented in various forms of hardware, software or combinations thereof. Preferably, these elements are implemented in software on one or more appropriately programmed general-purpose digital computers having a processor and memory and input/output interfaces.

In the preferred embodiment, the invention is implemented in software. This invention can be, but is not limited to being, embedded in firmware, resident on microcomputer, microcode, etc. Other embodiments may be entirely hardware, entirely software, or a combination of hardware and software elements.

Additionally, the present invention can be in the form of a software product stored or accessible from any computer usable medium providing computer program code. This includes, but is not limited to any apparatus that may store, communicate, or propagate the program for use by or in connection with, any device capable of program execution. The medium may be optical, electronic, magnetic, electromagnetic, a transmission medium, or a semiconductor medium. A computer readable media may be embodied as a computer hard drive, removable computer disk, random access memory, read only memory, semiconductor or solid state memory device, magnetic tape, punch card, or optical disk. Current examples of optical disks include Compact Discs (CDs), Digital Video Discs (DVDs), High Definition DVDs (HD-DVDs), Laserdiscs, Blu-Ray Discs, Minidiscs, or magneto-optical discs. With the exception of Laserdiscs, all of these disks may be in a fixed read only memory (ROM), recordable (±R), or recordable/rewriteable (-RW) format.

A data processing system may be comprised of one or more processors with supporting electronic devices such as a motherboard. These processors may include memory resident on the processor or connected via a system bus to local memory, cache memory, or shared system or network memory. The data processing system may be coupled to input devices such as keyboards, voice recognition technology, including microphone and associated voice recognition software, or pointing devices such as mice, trackballs, light pens, or touchpads. These inputs may be used singly, or in combinations of two or more. The data processing system may also be coupled to output devices that may include CRT or LCD monitors, digital projectors, printers, or even audio output, e.g. a voice synthesizer to output spoken information. The data processing system may also include communications adapters such as network cards, modems, or networking backplanes.

Network adapters that may be included in a data processing system allow data to be transferred across an intervening public or private network to and from other terminals, servers, printers, or remote storage devices. Some current examples of network adapters are Ethernet adapters, wireless WiFi and WiMax adapters, token ring adapters, etc. Current networks include Local Area Networks (LANs), Wide Area Networks (WANs), the Internet, ad hoc networks, direct connect networks or virtual private networks (VPNs).

Electronic documents may be comprised of stand-alone electronic documents in an electronically recognizable format. This may include Microsoft Word documents, rich text files, ASCII text files, binary data files, etc. Electronic documents may also include entries into relational databases, fixed record format database, and non-relational databases. Current examples of relational databases include Microsoft SQL Server, Oracle Database server, Sybase, IBM DB2 databases, MySQL databases, PostGre SQL databases, and Microsoft Access. A current example of a fixed record database is the Btrieve database. A Non-relational database is exemplified by simple hierarchical file storage.

A keyword may be a phrase comprised of one or more words meant to be treated as a single term.

A thesaurus for expanding keywords is comprised of a list of keywords, each of which may have one or more thesaurus entries containing words or phrases defined to be keyword "synonyms". Each keyword, synonym or relation between keyword and synonym may be entered manually or generated in an automated fashion.

Referring now to the drawings in which like numerals represent the same or similar elements and initially to FIG. 1, a profile matching system (100) consists of a series of discrete steps that allow a user to prepare, evaluate and manage profiles as requirement definitions are created and run against them. A document storage system (103) collects and stores unstructured documents to be distributed to the profile evaluation system (102).

Requirements, criteria, and keywords are entered into a requirement definition storage system (101). A requirement definition may be comprised of a request for document profile matching and a set of requirements for the profile match.

An exemplary embodiment of one preferred application for the present invention is used by an employment agency or corporate HR department to profile job applicant resumes. In this embodiment, a requirement definition consists of a job request and associated job requirements from an employer or hiring manager. The job requirements may include the type of employee sought, job definition, length of experience required, fields of experience required and other job prerequisites. This requirement definition, or job request, may be entered into the requirement definition storage system (101) by the employer, employment agent or corporate HR department, directly from a workstation or over a communication network such as the internet or a LAN.

After one or more requirement definitions are entered into the requirement definition storage system (101), the requirement definitions are sent to the profile evaluation system (103). In one embodiment, requirement definitions may be stored in a database for execution pending readiness on the part of the profile evaluation system (103). Tasks may also be sent directly from the requirement definition storage system (101) to the profile evaluation system (103) over a network, system bus or within computer memory. Another embodiment may allow the requirement definition to remain in memory space with a pointer or reference to the applicable memory space passed to the profile evaluation system (103).

The profile evaluation system (103) applies any factors required by the requirement definition to any applicable profiles. These factors may include requirements specified when a requirement definition was entered. In the preferred embodiment, these requirements may include education, job, or industry experience requirements. In the present embodiment, resumes may be searched for relevant keywords, a profile score generated based on keywords found, and the resumes categorized, ranked and viewed or excluded from view based on their profile score.

After evaluating the candidate documents, those meeting the requirement definition threshold are contacted and then placed into the profile pipeline system (104).

Any number of user workstations (107) may be connected via a communication network (106) to the requirement definition storage system (101), document storage system (103), profile evaluation system (102), and the profile pipeline system (104).

The communications network (106) allows users to add requirement definitions to the requirement definition storage system (101) or upload documents into the document storage system (103) through workstations (107). Additionally, user workstations (107) can connect to the profile evaluation system (102) via a communications network (106), allowing users to monitor requirement definitions and profiles as evaluations are being performed.

Users may also connect to the profile pipeline system (104) through the communication network (106) to administer matched requirement definition/profile lists and to facilitate communication between parties involved. After profile has been approved by a system administrator, profile information is aggregated into a candidate list and sent to a client (105).

In the exemplary embodiment, candidates may submit their resume, which is stored in an unstructured, original format in the document storage system (103). Candidates may electronically transmit their resumes directly to an employment agency's or corporate HR department's document storage system or submit a paper copy of their resume to the employment agency or corporate HR department, which may then be manually entered into document storage. The employment agency or corporate HR department may also use an automated means, such as scanning and conversion via OCR (optical character recognition), to convert the paper resume to a digital format before saving it to electronic document storage (103). Resumes may also be collected by an employment agent or corporate HR department from publicly available information, employment websites, or other online postings. Other resume sources include, but are not limited to, an employment agency's or corporate HR department's own in-house resume archives, a partner agency's or partner corporate HR department's resume archives, or resume referrals.

When an employer (i.e. client), submits a job description and request for candidates to the employment agency or corporate HR department, the requirement definition is entered into the requirement definition storage system (101). Candidates may then have the opportunity to apply for a listed job, indicating they are interested in being considered for the job. In order to generate a larger pool of qualified candidates, previously gathered or archived candidate resumes may also be automatically profile matched for a requirement definition.

Each job candidate's profile would then be evaluated in the profile evaluation system (102), and a rating or category assigned. Job candidate profiles that pass the initial screening in the profile evaluation system (102) are contacted and then forwarded to the profile pipeline system (104). This screening process allows automated filtering, ranking and processing of a large number of job openings and candidates. Employment agents or corporate HR departments can then concentrate on developing the selected candidates for presentation to the employers.

The profile pipeline system (104) allows multiple users to input or view data on selected candidates. In one embodiment, the profile pipeline system (104) is used to track candidates for jobs, keep working notes on each applicant per job, and organize the vetting and presentation process. The profile pipeline system (104) can also be used to view information regarding specific jobs. For example, employment agents or corporate HR departments may pick a particular job and "drill down" to view individual applicant information such as candidate history, contact information or their resume. Employment agents or corporate HR departments may also use the profile pipeline system (104) to note that they have interviewed a prospective candidate regarding the job or view notes on resume formatting procedure for a particular job. An agent or corporate HR department may even use the profile pipeline system (104) to add a note to the database marking a job candidate as "not for this job", removing the candidate from the pipeline for a particular job or position.

In this embodiment, changes made by an employment agent or corporate HR department on one user terminal (107) may be transmitted to other users via email on a regular basis. In another embodiment, changes and notes applied profile pipeline data may be tracked manually, or through a shared resource such as a centralized database.

Once the most promising candidates for a job are identified, the candidate profile information is passed to the employer or hiring manager (105) for consideration.

Other embodiments of this system may include: matching profiles for an online dating system; verifying academic paper originality; restaurant or recipe selection; or vendor selection; or landscape design and architecture.

FIG. 2 illustrates a general overview of the profile evaluation system (102). Criteria, requirements, traits, characteristics, keywords and relevant phrases associated with each requirement definition are entered into a requirement definition management module (204). Relevant keywords and phrases for each requirement definition are evaluated by the keyword module (202) before execution.

Unstructured electronic documents are entered into document storage (201). Prospective candidates may electronically submit documents to document storage (103) or documents may be gathered and entered manually or automatically by a profiling agent.

Likely candidates for profiling are then identified for each profiling requirement definition. Candidates, through the requirement definition management system (204), may be given the opportunity to express their interest in having their profile evaluated for each requirement definition. Additionally, candidates may be selected automatically by a profiling agent or corporate HR department from previously run requirement definitions, or from publicly or privately available information.

When a requirement definition is executed, the requirement definition and associated keywords and phrases are loaded from the requirement definition management module (204) and keyword module (202) into the profiling module (203). The profiling module (203) then loads documents for candidates being considered for the active requirement definition from document storage (201). After the profiling module (203) matches each electronic document's profile against the requirement definition requirements, the matching profiles and keywords are evaluated in the weighting module (205). The weighting module (205) applies a weight or importance to each keyword or phrase found in an applicable profile. The profile and weighted keyword assessment then passes to the ranking module (206), where the profiles are ranked and categorized based on the weighted keyword assessments.

In the preferred embodiment, candidate resumes are stored in a document storage system (103) comprised of a database. This resume storage system may reside on a shared access, central computer, server, or stand-alone workstation.

The document storage (201), keyword module (202), profiling module (203), requirement definition management module (204), weighting module (205), ranking module (206), and profile pipeline system (104) may exist as stand-alone modules, or one or more modules may be included together in one piece of software. Different systems and modules may be stored on one or more computers, which may be connected to a computer network. Single or multiple instances of each module or system may communicate with single or multiple instances of other modules or systems residing on the same computer workstation or server, or communicate across a network to separate computer workstations or servers.

FIG. 3 illustrates the detailed process implemented by the profile evaluation system (103). In this detailed process, the requirement definition management module (204) generates a list of candidates being considered for a profile match (304).

In the exemplary embodiment, an employer or hiring manager might submit a job listing to an employment placement agency or corporate HR department. The employment agent or corporate HR department would submit the job request as a requirement definition to the requirement definition management module (204), along with a set of associated keywords and phrases to the keyword module. For example, if an employer were seeking to hire a computer programmer, an employment agent or corporate HR department would submit the open computer programming position to the requirement definition management module (204). When the computer programming job opening is publicized, likely candidates may submit a request to be considered for the open position (302). Additionally, an employment agent or corporate HR department may mark previously gathered or submitted resumes for profile matching on the computer programming job. These requests are accessed by the requirement definition management module (204) to generate a list of candidates for profile matching (304).

The keyword module (202) generates a list of keywords applicable to an associated requirement definition (301). The keyword module (202) then uses a thesaurus to generate an expanded keyword list (305). In one embodiment, the keyword module (202) would generate, through either manual input or an automated process, a list of keywords associated with the computer programming job (301), e.g. "C/C++", "Visual Basic" or "Java". In order to properly evaluate an unstructured document, the keyword module may then expand the keyword list using a thesaurus (305). For the computer programming job exemplified above, the keyword module (202) may use the thesaurus to expand the keyword "C/C++" to include "C programming language", "C++", "C#", or the term "Visual Basic" may be expanded to include "VB", "VB.Net", or "VB v6.0". Other examples may include expanding more general terms such as the phrase "computer programmer" to include terms such as "systems analyst", "programmer", "software developer", etc.

In another embodiment, such as profiling in an automated matchmaking/dating system, the keyword module (202) may expand a general keyword such as "outdoors" to include more specific terms such as "camping", "hiking" or "kayaking".

Once a candidate list is generated (304), the profiling module (203) loads the required documents from document storage (303), then applies the expanded keyword list to the retrieved documents (206).

In this preferred embodiment, the profiling module (203) loads the required resumes then searches each document for instances of keywords and phrases from the expanded keyword list (306). The profiling module (203) would then track the keywords found in each unstructured document.

In other embodiments, the profiling module may also track the number of times a keyword was found in a target document, the context the keyword appeared in, each keyword's relation to other keywords in the document, or the number of keywords found.

After the keyword list is applied to the target documents (306), the profiling module (203) separates the qualifying and non-qualifying documents, generating a list of qualifying documents that meet a minimum threshold (307) and another list of documents that did not meet a minimum threshold (308).

In one embodiment, the profiling module (203) generates a list of job candidates that meet some minimum threshold on their resume. Referring to the example above, an employer seeking a C++ computer programmer would have a requirement definition requiring some prior C++ computer programming experience. In that case, the minimum threshold would be some occurrence of the keyword "C++" or its thesaurus defined synonyms. Resumes with at least one occurrence of "C++" or its synonyms would be considered at least minimally qualified for the C++ programming position.

In this embodiment, the profiling module (203) also generates a list of documents that did not qualify under the requirements (308). For example, if an employer were to set requirements for a job so stringently that no candidates were qualified, the employer would be able to see what factors most often caused candidates to be rejected. This allows employment agents, corporate HR departments and employers to finetune their job requirements and evaluate compensation plans for niche employment markets.

Referring again to FIG. 3, the weighting module (205) generates a keyword weighting scheme (309). This weighting scheme is described in further detail below, but may assign varying levels of importance or weight to words in the keyword list. Keywords may also be split into one or more distinct groups. Each keyword group may have an associated score based on the statistics of the keywords in the target document.

In the exemplary embodiment, the keyword weighting scheme contains at least 4 groups; 1) Industry Specific Keywords, e.g. "financial industry" or "insurance underwriting", 2) Job Role Keywords, e.g. "developer" or "business analyst", 3) Primary Technology Keywords, e.g. "C#", "C++", "WebSphere" and "WebLogic", and 4) Difficult to Find Required Skills, e.g. "embedded software", "Oracle database administration", "80×86 assembly language".

Other embodiments may include, but are not limited to, categories such as Secondary Technology Keywords, e.g. "HTML" and "Javascript", Secondary Job Duties, e.g. "customer service", "technical support", or Hardware Certifications e.g. "CNA" or "A+ certification".

The weighting module (205) then applies the various weights to the keywords found in the target documents (310). In one embodiment, the weights assigned to each keyword by the weighting module (205) (weighting scheme 309) may be comprised of a system that evaluates the frequency, including the presence or absence, of keywords, the context of keywords, the number of keywords, or the relations of keywords to other keywords or the context of keywords in a document. It should be understood that evaluating the frequency of keywords may include noting that a particular keyword did not appear in a document, achieving a frequency of zero.

An exemplary embodiment of this weighting scheme would be where the first occurrence of each keyword from a group is assigned one point value, and subsequent occurrences of each keyword are assigned lesser values. For example, the first instance in a resume of the keywords "WebSphere" and "WebLogic" may each be assigned 1 point, and any successive occurrences assigned ½ point. The weighting module (205) may then round numbers up or down to the nearest whole integer.

In this embodiment, a weighting module (205) might evaluate a resume containing 3 instances of the keyword "WebSphere" and 2 instances of "WebLogic". The weighting module would assign 1 point for the first occurrence of the keyword "WebSphere", and ½ point each for the second and third occurrences, for a total of 2 points. The weighting module (205) would also assign 1 point for the first occurrence of "WebLogic", and ½ point for the second occurrence for a total of 1½ points. This would then be rounded down to 1 point. Totaling the points for the "WebSphere and "WebLogic" keywords, the weighting module would assign a score of 3 points in the Primary Technology Keyword category.

In other embodiments, the weighting module (205) may assign a decreasing point value for each occurrence of a keyword, i.e. 1 point for the first occurrence of a keyword, 0.9 points for the second occurrence, 0.8 points for the third, 0.7 for the fourth, etc.

Additionally, the weighting module in this embodiment separates the scores for each category. Referring to the example categories listed above, a resume assigned 2 points in category 1 (Industry Specific Keywords), 4 points in category 2 (Job Role Keywords), 3 points in category 3 (Primary Technology Keywords), and 2 points in category 4 (Difficult to Find Required Skill Keywords) would be calculated to have a weighted profile score of 2432, with each digit in the weighted score representing a separate keyword category.

In some embodiments, each digit in the weighted score may be normalized against an ideal score to generate a "relative score". This relative score can be used to quickly determine how closely a candidate comes to achieving an ideal score.

For example, each score in each category may be normalized so that the ideal relative score in each category is indicated by a 5, resulting in an ideal relative score of 5555. This relative scoring allows a user to evaluate the ideality of a candidate for a particular position without referring back to the original requirement definition. Relative scores above 5 in each category indicate that a candidate is overqualified, while relative scores lower than 5 indicate that a candidate is underqualified. A candidate with a weighted score of 3523 being evaluated against a requirement definition looking for an ideal score of 2472 may be given a relative score of 6626. This relative score indicates that the candidate is slightly over qualified in categories 1, 2, and 4, and well underqualified in category 3.

In some embodiments, the relative score in each category may be calculated using the formula: $5-[\text{ideal score}-\text{actual score}]/\text{ideal score} \times 5$. Other embodiments may include, but are not limited to, other statistical normalization formulae, recentered percentage formulae, central limit theorems or standard deviation formulae.

After each document's profile has been weighted by the weighting module (205), the ranking module (206) generates a category definition and ranking scheme. This category definition and ranking scheme is then applied by ranking module (206) to categorize and rank documents (312) based on criteria specified by the user.

In one embodiment, categorizing applicants based on their profile allows an employment agent or corporate HR department to present groups of candidates based on objective experience criteria. Employers can specify requirements that are "must have", and differentiate them from requirements that would be "nice to have", but are not required.

An exemplary categorization scheme may include categories such as "Overqualified", "Senior HotList", "A-List", "Presented List", and "Applied". Based on the employer requirements and the keywords used, the employment agent or corporate HR department may set thresholds for qualifying for each list. For instance, using the four category weighted profile score described above, job candidates scoring over 4772 may be put on the Overqualified list, over 3332 may be put on the Senior HotList, over 2331 on the A-List, over 0231 on the Default List, with actual qualifying applicants being put on the Applied List, and arranged next to the job for which they applied. Referring to the scoring example above, if an applicant were to receive the weighted profile score shown above, 2432, she would be placed on the A-List. Had she received a score of 3432, she would have been placed on the Senior HotList.

Once candidates are categorized based on their weighted profile scores, they are ranked against other candidates in the same category (312).

In some embodiments, candidates may then be sorted by individual category score, i.e. candidates may be ranked by a single digit in the profile score. Additionally, employment agents or corporate HR departments may filter candidates based on properties of their resume. One or more categories in a candidate's profile score or any other employment agent or corporate HR department entered category may be used to filter a candidate (i.e. include or exclude a candidate as a match for the job).

In one embodiment, an employer may prefer one category over another. For example, using the categories described above, Candidate A, with a varied technology background would most likely have a resume with a wide variety of Primary Technology Keywords, scoring high in category 3, with a theoretical score of 2372. Candidate B, with extensive experience in a particular field such as the financial industry, would have a resume containing many Industry Specific Keywords, scoring high in category 1, with a theoretical score of 4342.

An employer may prefer to see candidates with a varied technology background over candidates with extensive experience in a particular industry. In such a case, an employment agent or corporate HR department would define a ranking scheme where profile scores with a high category 3 score, in Primary Technology Keywords, was ranked above profile scores with a high category 1 score, Industry Specific Keywords. In the above example, Candidate A would be a more suitable match to present to the employer or hiring manager.

In other embodiments, categories may not be specified at all. Qualified applicants may simply be ranked based on the document profile keyword ratings.

In situations where a relatively large number of candidates are considered qualified for a position, an employment agent or corporate HR department may find it useful to narrow the list of candidates an agent or corporate HR department concentrates on developing. This may be accomplished by overriding the normal view of the ranked candidate list. In this embodiment, an employment agent or corporate HR department may override, or filter out, candidates with a score above or below a certain threshold. Using the previous example, if 40 candidates were to qualify for a position, the employment agent or corporate HR department may find it advantageous to override the view of the ranked list by filtering out any candidate with a score of 3 or less in one of the profile score categories.

An employment agent or corporate HR department may also categorize candidates in ways not related to scoring, such as extent of a candidate's work experience in a certain field, and later override the ranked list to view candidates in a certain category. For example, an employment agent or corporate HR department may wish to see only candidates that have experience developing software for the financial industry, and filter out candidates with no financial industry experience.

In other embodiments, employment agents or corporate HR departments may assign candidates to a predefined field when entering the candidate into the profile matching system. For example, an employment agent or corporate HR department may place a candidate into a general work experience category such as Finance, Non-Finance, or Consultant, or Job Role categories such as Programmer, Project Manager or Network Engineer. Ranked results may be overridden to show candidates that an employment agent or corporate HR department had previously noted to be well suited for work in a particular field.

In yet another useful embodiment, candidates may be assigned to a category based on the number of years worked in a particular field, years since graduation, or years of management experience. Ranked results may be overridden to show only those candidates that have been previously noted to fall within certain guidelines, i.e. 3-5 years since graduation, 2+ years of management experience, etc.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:

1. A method for providing profile matching within an unstructured electronic document having been recorded on a computer-readable medium, the method steps comprising:
   loading one or more unstructured electronic documents from storage;
   defining a set of requirements to be met by each of the unstructured electronic documents, said defining further comprising creating list of keywords from the defined set of requirements and defining a set of one or more synonyms represented by each keyword;
   calculating a degree of conformance of each of the unstructured electronic documents containing one or more of the defined set of one or more synonyms each containing one or more criteria; and
   rating each of the unstructured documents by assigning one or more profile scores indicating a document's calculated degree of conformity to the one or more defined synonyms represented by each keyword.

2. The method according to claim 1, wherein the defining of one or more synonyms is performed using a thesaurus, wherein the thesaurus contains synonyms added via using at least one method selected from a group consisting of:
   previously defined lists of synonyms; and
   user defined addition of synonyms.

3. The method according to claim 1, wherein the comparing is comprised of searching an unstructured document for criteria matches wherein searching includes at least one method selected from a group consisting of:
   evaluating the presence of synonyms in a document,
   evaluating the absence of synonyms in a document,
   evaluating the frequency of synonyms in the document,
   evaluating the context of synonyms in the document,
   evaluating the relationship of synonyms to other synonyms in the document and
   evaluating the number of synonyms in the document.

4. The method according to claim 1, wherein the calculating is comprised of generating a list of qualified documents based on meeting or surpassing a predefined score threshold corresponding to the set of synonyms represented by each keyword.

5. The method according to claim 4, wherein the generating includes tracking statistics associated with the documents' degree of conformity to a predefined score threshold.

6. The method according to claim 1, wherein the calculating includes generating a list of non-qualified documents based on failure to meet or surpass one or more user defined requirements.

7. The method according to claim 6, wherein the calculating includes tracking the requirements each document failed to meet which in turn caused the document to be defined as non-qualifying.

8. The method according to claim 1, wherein assigning profile scores includes generating a profile score by assigning points to a document based on one or more statistics selected from a group consisting of:
   the absence of synonyms in the document,
   the presence of synonyms in the document,
   the frequency of synonyms in the document,
   the context of synonyms in the document,
   the placement of synonyms in the document,
   the relationship of synonyms to other synonyms in the document, and
   the number of synonyms in the document.

9. The method according to claim 8, wherein assigning points includes assigning a point value for the first occurrence of each synonym in a document, and lesser point values for subsequent occurrences of synonyms in the document.

10. An automated method of scoring one or more unstructured electronic documents having been recorded on a computer-readable medium, the method comprising the steps of:
    searching for synonyms represented by keywords in unstructured electronic documents;
    assigning one or more point values for statistics related to the synonym occurrences in each of the documents, said assigning including weighting a profile score by assigning one or more numeric point values to the unstructured electronic document based on the frequency of each synonym's appearance in the document; and;
    ordering the point values in a predetermined manner to generate a multi-digit profile score where each digit represents a point value of each occurrence of each synonym.

11. The method according to claim 10, wherein assigning one or more point values includes one or more methods selected from a group consisting of:
    assigning fixed point values for each occurrence of each synonym in the unstructured electronic document,
    assigning a first point value for the first occurrence of each synonym in the structured electronic document, and a lower, fixed point value for each subsequent occurrence of each synonym, and
    assigning a first point value for the first occurrence of each synonym in the unstructured electronic document, and decreasing point values for each subsequent occurrence of each synonym.

12. The method according to claim 10, wherein assigned point values are aggregated into one or more categories to generate a profile score including one or more profile score categories.

13. The method according to claim 12, wherein the profile score in each category is normalized to generate a relative score reflecting the correlation between the desired and actual profile score in each category.

14. The method according to claim 10, wherein the categorizing includes separating one or more unstructured electronic documents into one or more document categories based on one or more profile score categories.

15. The method as recited in claim 10, wherein the assigning to a category includes listing in order two or more unstructured electronic documents from a category into a list, the ordering based on profile score.

* * * * *